United States Patent [19]

Gotfried

[11] Patent Number: 5,429,641
[45] Date of Patent: Jul. 4, 1995

[54] SURGICAL DEVICE FOR CONNECTION OF FRACTURED BONES

[76] Inventor: Yechiel Gotfried, No. 10 Ben Gurion Avenue, Kiryat Bialik, Israel

[21] Appl. No.: 170,529

[22] Filed: Dec. 20, 1993

[30] Foreign Application Priority Data

Mar. 28, 1993 [IL] Israel .................................... 105183

[51] Int. Cl.⁶ ...................... A61B 17/76; A61B 17/90
[52] U.S. Cl. ...................................... 606/67; 606/104; 606/96; 606/73; 606/69; 411/383; 411/410
[58] Field of Search ................... 606/60, 65, 69, 72, 606/73, 86, 96, 97, 104, 67; 411/383, 410; 81/459, 436, 461

[56] References Cited

U.S. PATENT DOCUMENTS

| 4,465,065 | 8/1984 | Gotfried . |
| 4,940,467 | 7/1990 | Tronzo ................... 606/73 |
| 5,176,681 | 1/1993 | Lawes et al. ............ 606/65 |

FOREIGN PATENT DOCUMENTS

| 2501033 | 9/1982 | France ................... 606/69 |
| 670125 | 5/1989 | Switzerland ........... 411/389 |
| 2232218 | 12/1990 | United Kingdom ................ 411/410 |

*Primary Examiner*—Tamara L. Graysay
*Attorney, Agent, or Firm*—Frishauf, Holtz, Goodman & Woodward

[57] ABSTRACT

A surgical device for percutaneous connection of a fractured upper part of the femur to the shaft comprises: a connector plate with a lower straight portion for screwed connection to the femur shaft and with a sharp bottom end for insertion through a small skin incision, having its upper portion perforated by two oblique, tapped bores for fixation of two long screws serving for connection of the fractured parts. Each screw has a wood-screw-shaped inner end and a cylindrical shaft with a hexagonal recess at its outer end which is continued by a tapped bore. Each screw is slidingly positioned in a sleeve which has its outer end slotted and screw-threaded for fixation in the oblique bores of the plate. The connector plate is positioned and fastened to the femur by an angular connector arm composed of a short horizontal arm for firm perpendicular connection to the top of the plate by a long screw, and a vertical portion parallel to the plate provided with bores coaxial with the bores in the plate for guidance of the screws. A screwdriver contains a central shaft having a screw-threaded inner end for engagement with the tapped bores in the screw ends, an intermediate tubular shaft having its inner end hexagonally shaped for engagement with the recesses in the screw ends, and an outer tubular shaft provided with teeth for engagement with the slots in the sleeve ends. All three shafts can be independently rotated and axially moved by separate grips at the outer end of the screwdriver.

16 Claims, 8 Drawing Sheets

FIG. 17a

SURGICAL DEVICE FOR CONNECTION OF FRACTURED BONES

BACKGROUND OF THE INVENTION

The present invention is an improvement of the surgical device disclosed in my U.S. Pat. No. 4,465,065. It serves for connection of the fractured neck to the shaft of a femur by means of a pre-drilled connector plate, without the requirement of making a large incision in the overlying skin and tissue.

The connector plate according to the above patent and according to the present invention has a sharp lower edge by which it penetrates through a small incision in the trochanter region into close contact with the shaft. During the operation the plate is temporarily attach to the horizontal portion of a connector arm, while its vertical portion extends parallel to the plate and is provided with holes which are coaxial with the holes in the plate. Concentric guide tubes are inserted through the holes in the vertical portion of the connector arm, are pushed through the soft tissue up to the plate and serve as guides for pre-drilling of the bone parts in the correct position as viewed by X-ray equipment. After pre-drilling the inner guide tubes are removed and the outer tubes serve for insertion of long screws, and are afterwards removed. The long screws are tightened so as to contract the fractured parts. Short screws serving for firm attachment of the plate to the femur shaft are now inserted through the vertical portion, of the connector arm, after suitable drilling through tubes inserted into holes in the arm, which are, co-axial with the holes in the plate. The connector arm is now detached from the plate, and the wound is closed.

The present device is similar and serves the same purpose, but is designed to avoid certain drawbacks of the original device which have come to light during its use in operations of the kind referred to. The following main drawbacks were observed:

The long screws did not permit active compression of the fractured bone parts, a task which is most important for quick healing of the bone and for early use of the limb by the patient.

The long screws were not sufficiently guided in the holes of the connector plate and were apt to wobble, often resulting in instability of the fracture after connection.

The screws were apt to protrude out of the bone into the soft tissue, after walking of the patient had started and the fracture had been pressed.

The connector plate was not firmly fastened to the femur during operation, which made drilling difficult.

The device according to the present invention aims to obviate these drawbacks by providing improved components which facilitate and shorten the progress of the operation on the one hand, and hold the fractured parts in full alignment and under compression after their complete jointing, on the other. In addition, sufficient space is provided for axial sliding out of the connecting screws, while preventing their protrusion out of the connector plate.

SUMMARY OF THE INVENTION

Before going into constructional details of the device, it should be noted that the following directional expressions will be employed in respect of the femur bone, the tool, the connector plate and the screws during the operation: the expressions "top" and "upper portion" of any part will refer to the femur top, and the "bottom" or "lower portion" will refer to the direction towards the knee joint. The expression "inside" or "inner portion" will refer to parts close to the bone outside or pointing towards it, while the expression "outside" or "outer portion" will refer to those parts which are outside the human body operated on, or pointing away from the bone. The improved surgical device for connecting and securing the fractured neck to the femur shaft includes:

A. Components which are to remain in the body after completed operation:
1. A connector plate of substantially rectangular cross section comprising a straight lower portion which has a sharpened lower end permitting it's insertion through a small incision in the skin and its being pushed through the soft tissue along the femur into its final position. Its upper end is short and bent outwardly to conform to the contour of the bone; it is perforated by a screw-threaded bore and at least one straight bore which serve for its connection to a holding tool. The upper part of the straight portion is perforated by two obliquely directed and screw-threaded bores, and the lower part is perforated by two or more straight, countersunk bores, all of which are used for guiding the drills for pre-drilling of the bone parts and for insertion of screws for firm attachment of the plate to the femur shaft and for connection of the fractured bone parts.
2. Two long screws used for connecting the fractured parts to the connector plate have their outer ends firmly guided and lengthwise and rotatably movable in relatively short sleeves; they extend through the upper bores through the femur neck and are screwed into the head portion; The outer ends of the sleeves are firmly held in the screw-threads of the two upper bores of the plate, thereby keeping the screws in firm position, while permitting axial movement; the outer ends of the screws are recessed each comprising a coaxial recess of hexagonal or other polygonal cross section which is continued by a screw-threaded bore. The inner ends of the sleeves are slightly crimped preventing the screws from escaping out of the sleeves by contact with a step on the screws.
3. Two or more short screws securing the lower plate portion to the femur shaft, having their heads hidden inside the counter-sinks.

B. Auxiliary equipment for insertion and fixation of the permanent components:
1. An angular connector arm, including a short horizontal portion for connection to the upper end of the connector plate and a longer vertical portion extending parallel to the direction of the connector plate; the vertical portion is perforated by two obliquely directed boresband by two or more straight bores, all of them coaxial with the bores of the connector plate, but of larger diameter, permitting the passage and fixation of guide tubes. It is preferably provided with set screws for locating the guide tubes and with means for attaching of an aiming device at its bottom end. The short horizontal portion is lengthwise perforated and contains a long screw and at least one protruding pin for engagement with the screw-threaded bore and the straight bore in the upper end of the connector plate.

2. Two long composite guide tubes of a length sufficient to extend through the bores in the connector arm to the corresponding oblique bores in the connector plate; they include an outer tube of an inner diameter corresponding to the diameter of the screw to be inserted and to be screwed into the fractured neck, and two inner, removable tubes, viz. a first tube concentrically bored to the diameter of a guide wire to be pushed therethrough into the bone, and a second tube concentrically bored to the diameter of a drill adapted to drill the bone for reception of the two long screws.

3. Two or more shorter guide tubes for insertion into the straight bores in the connector arm up to the corresponding bores in the connector plate serving for predrilling bone before final insertion of the screws for firm attachment of the connector plate to the femur shaft.

4. A special screw driver adapted for inserting and fixing the long screws and their sleeves in the connector plate and in the fractured bone parts, and for compressing the fracture after its connection.

The auxiliary equipment is removed from the body after the connector plate has been firmly connected to the femur shaft and the fracture has been connected and duly compressed by means of the long screws, whereafter the wounds are to be dressed.

The operation is carried out as described before in connection with the device disclosed in U.S. Pat. No. 4,465,065, with the difference that according to the present invention the long screws are axially movable, both active and passive, in their respective sleeves which have their screw-threaded ends firmly connected to the bores in the connector plate. This feature permits active compression of the fractured parts by the surgeon and preventing the drawback of the previous invention of gradual protrusion of the screw heads into the soft tissue with subsequent irritation and pains. In addition, the improved auxiliary equipment according to the present invention not only facilitates the operation, but requires less time than before, a boon both for the patient and the surgeon.

The manner and sequence of operating on a fractured femur neck will be described in detail with reference to the drawings showing the various permanent and auxiliary components of the device.

DETAILED DESCRIPTION OF THE DRAWINGS

Figure 1:
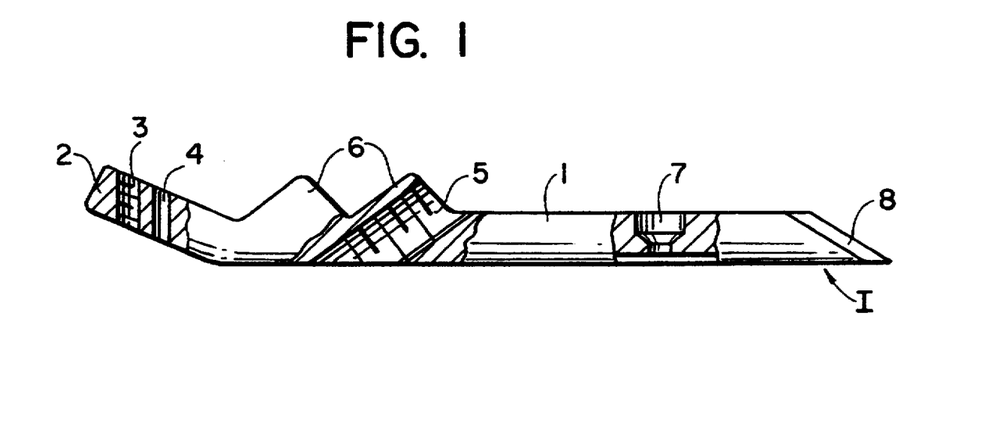
FIG. 1 is a side view and part section of the connector plate.
Figure 2:
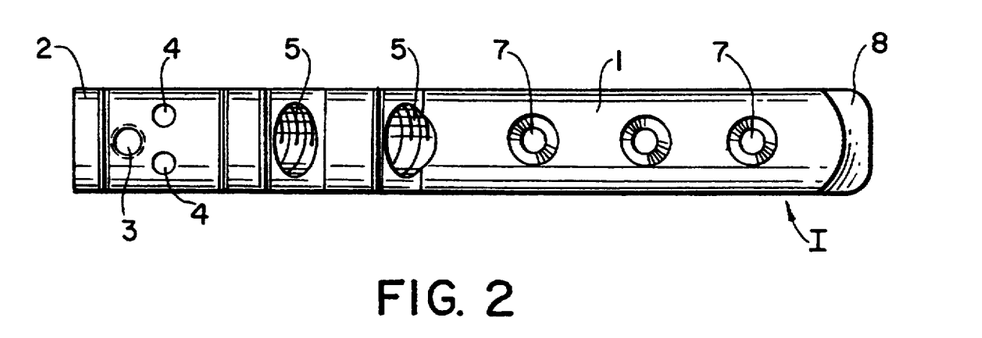
FIG. 2 is a plan view of the connector plate illustrated in FIG. 1.
Figure 3:
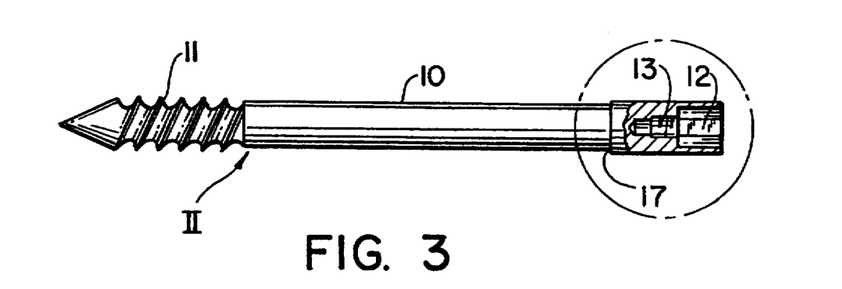
FIG. 3 is a side view of a long screw.
Figure 4:
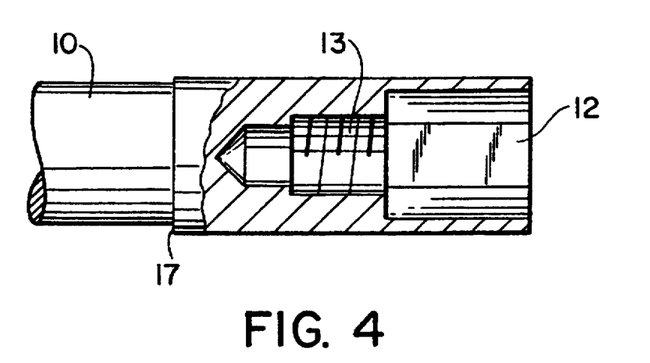
FIG. 4 is a section through the outer end of the screw illustrated in FIG. 3.
Figure 5:
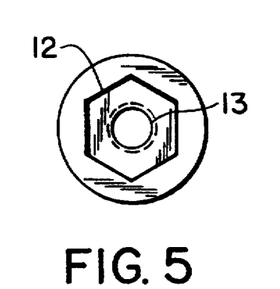
FIG. 5 is an end view of the screw illustrated in FIG. 3.
Figure 6:
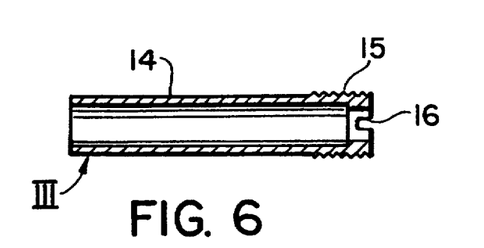
FIG. 6 is a longitudinal section of the sleeve covering the outer end of the long screw.

The connector plate I illustrated in FIGS. 1 and 2 includes a straight lower, main portion 1 and a head portion 2 outwardly bent in respect of the main portion, to conform to the contour of the bone. The head portion contains one larger, screw-threaded bore 3 and two smaller bores 4 for connection to the horizontal portion of the connector arm as will be described in detail further on. Next to the head portion two obliquely directed, screw-threaded bores 5 penetrate the main portion at an angle of about 130°, the outer surface of the portion being thickened by two lugs 6 permitting a greater length of the bores 5. Underneath the two bores 5 three countersunk bores 7 are drilled through the main portion at right angles thereto. The lower end of the main portion is sharpened (8) having the purpose of penetrating through the soft tissue and muscles close to the femur shaft during its insertion through a small cut in the skin.

Figure 7:
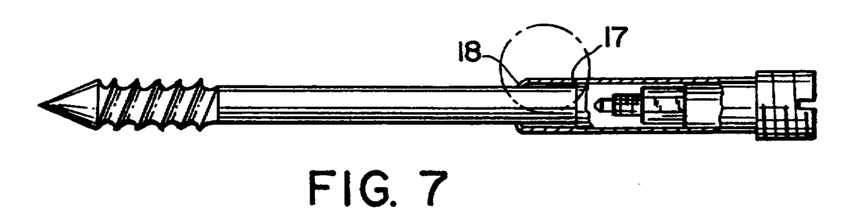
FIG. 7 is a side view and part section of the long screw positioned in the sleeve of FIG. 6.
Figure 7A:
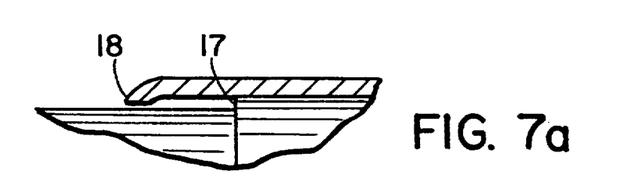
FIG. 7a is an enlarged section of part of screw II and sleeve III.

One of the two long screws II and its sleeve III is illustrated in FIGS. 3 through 7: Herein the screw includes a relatively long shaft 10, an inner end provided with screw thread 11 similar to that provided on wood screws, and an outer end recessed in the form of a hexagon 12 continued with a screw-threaded bore 13 of smaller diameter. The outer end of the screw is slidably, but tightly, inserted into the inner bore of a sleeve 14, which has its outer end provided with outside screw thread 15 and slotted by two or four slots 16 serving to engage the special screw driver to be shown in FIG. 11. The assembled screw and sleeve are shown in FIG. 7, part in side view and part in section. The inner end of the sleeve is inwardly crimped (18), thereby preventing the screw from sliding out of the sleeve by contact with a step 17 on the screw shaft. The three screws connecting the plate to the shaft of the femur by means of the three bores 7, are not shown as of the usual kind and size used in similar operations.

Figures 8, 9:
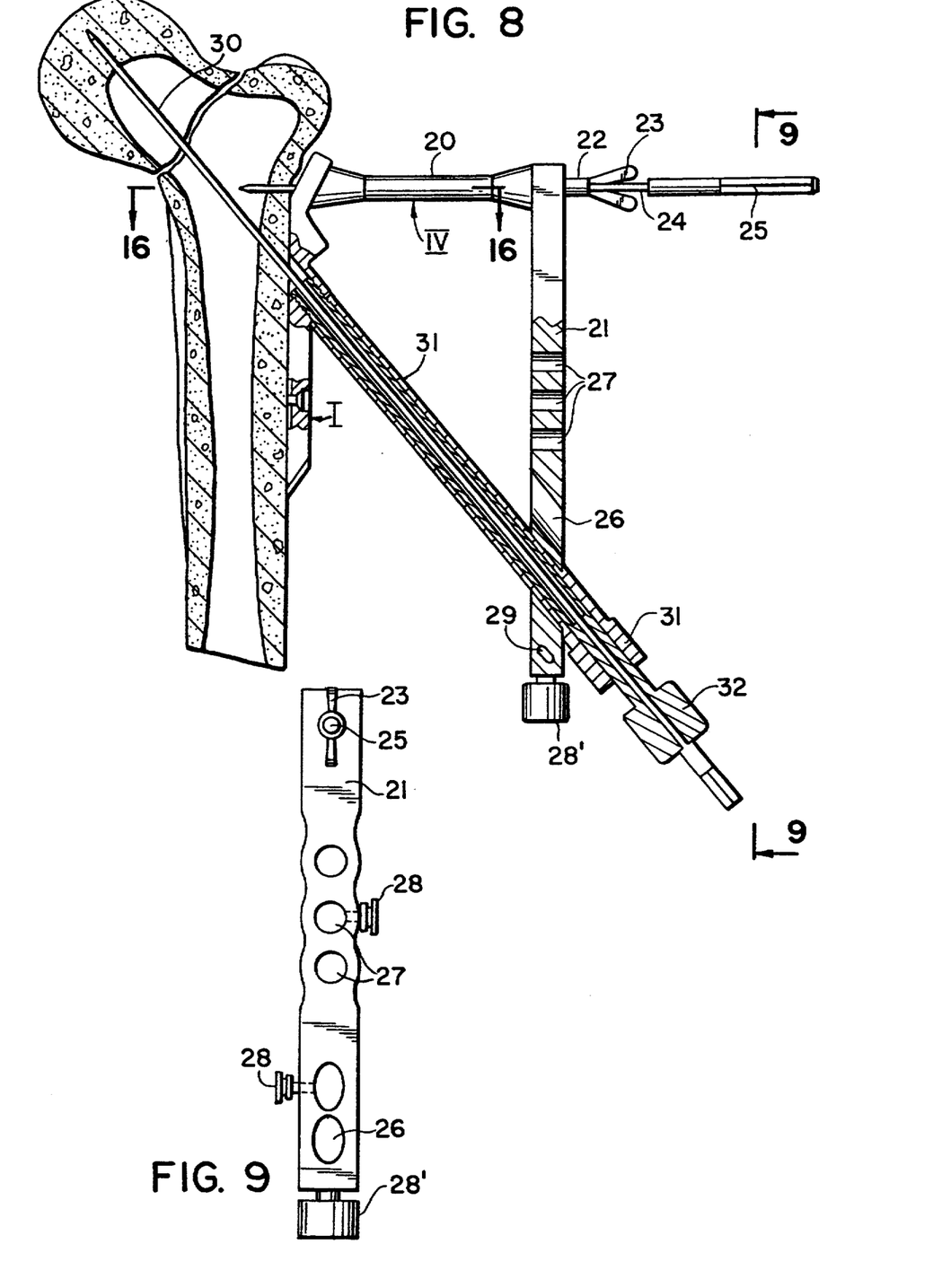
FIG. 8 is a sectional view of the connector plate, the connector arm and auxiliary equipment at the beginning of an operation.
FIG. 9 is an end view of the connector arm along line 9—9.
Figure 10:
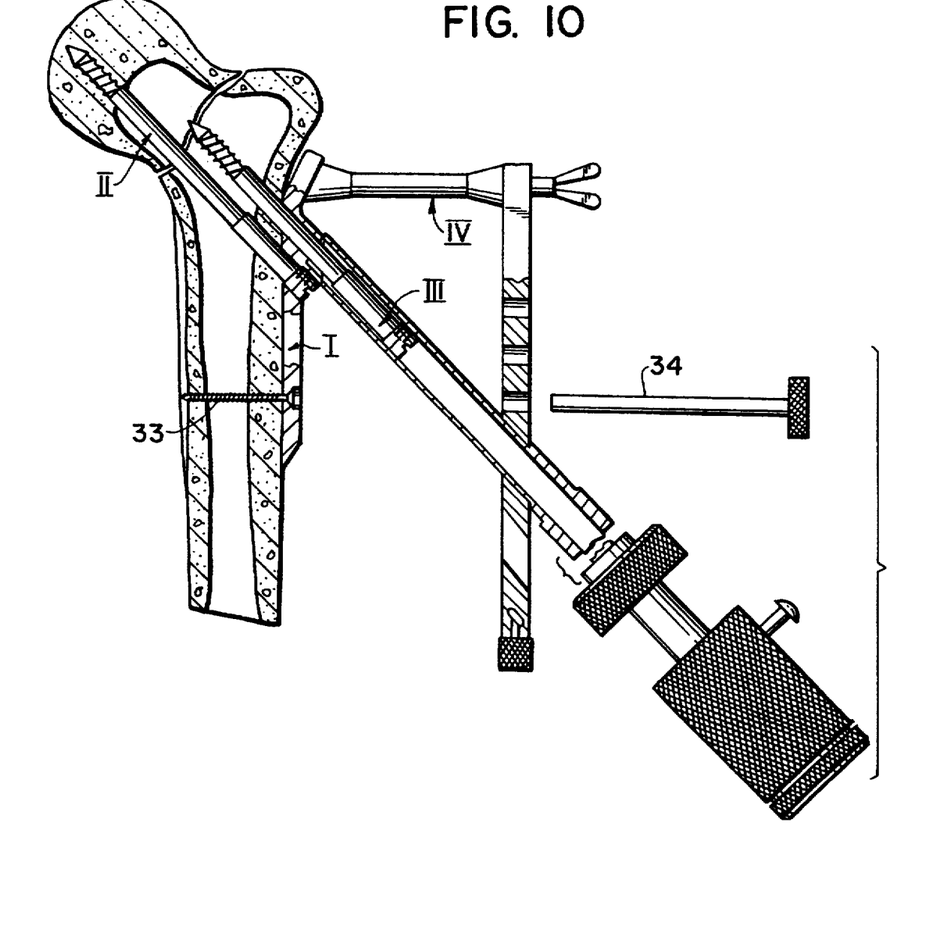
FIG. 10 is a sectional view of the connector plate, the connector arm, and the screwdriver, showing an advanced state of the operation, with one long screw and sleeve position and a second screw in its way to its final position.
Figure 10A:
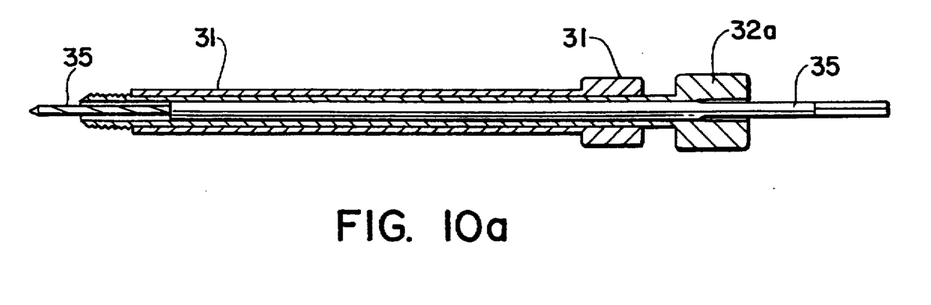
FIG. 10a is a longitudinal section of the second removable tube and the drill inserted in the main sleeve.
Figure 12:
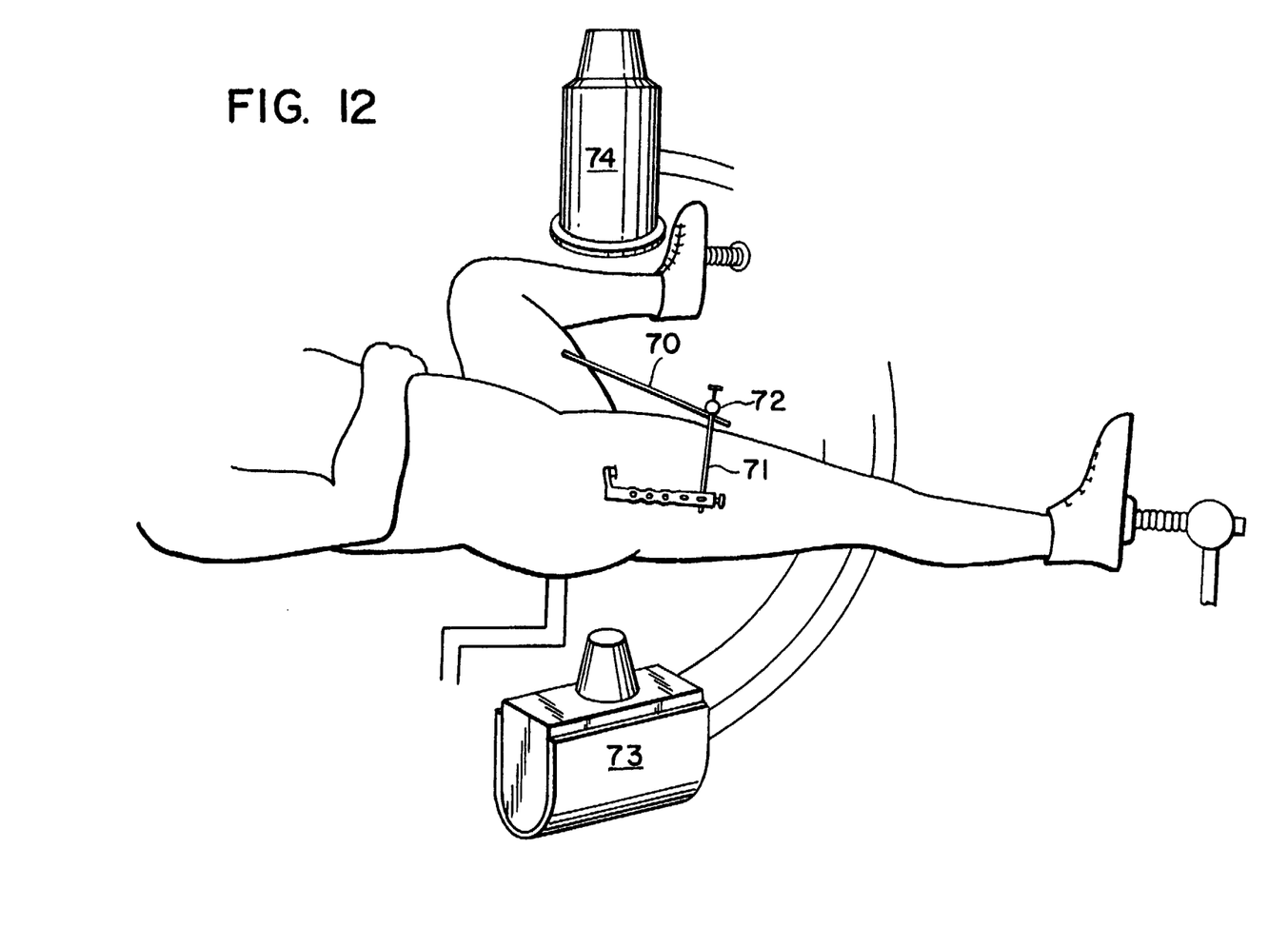
FIG. 12 is a drawing showing a stage of the operation while using a rod-shaped aiming device.
Figure 13:
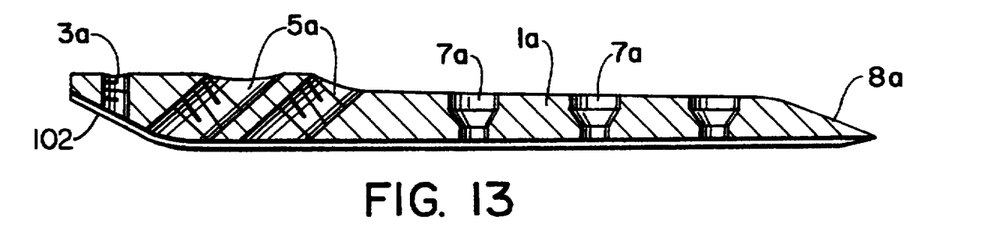
FIG. 13 is a side view and part section of a second embodiment of the connector plate.
Figure 14:
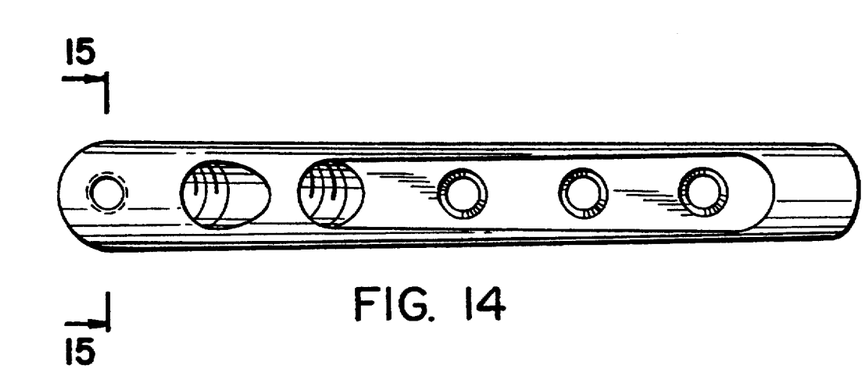
FIG. 14 is a plan view of the connector plate illustrated in FIG. 13.

FIGS. 8, 9 and 10 illustrate the auxiliary equipment serving for insertion and tightening of the long screws and for compressing the fractured bone parts after insertion of the screws. The main instrument is an L-shaped connector arm IV which includes a horizontal portion 20 and a vertical portion 21 firmly connected to each other at right angles. The horizontal portion is provided at its inner end with two pins (not visible) engaging the bores 4 of the connector plate and serving to ensure exact parallel alignment of the connector plate with the vertical portion. A connecting screw 22 extends through a central bore in the horizontal portion and connects the connector arm to the plate by engaging the screw thread 3 in the latter, being actuated by a grip 23. At the same time two pins enter the bores 4 and prevent relative rotation of connector plate and arm. The screw 22 is hollow to permit passage of a long, pointed bar 24 provided with a grip 25 for forceful insertion into the bone and for exact location of both the connector plate and the connector arm relative to the femur bone. The vertical portion contains two large, obliquely directed bores 26 which are coaxially aligned with the bores 5 in the connector plate, but of larger diameter, Above the two bores 26, three smaller bores 27 are drilled through the portion at right angles thereto and coaxially aligned with the bores 7 of the connector plate, Set screws 28 penetrate the sides of the bores 26 and 27 and serve to hold the tubular guides in position. An additional feature of the connector arm is in the form of an oblong hole 29 perforating the lower end of tile vertical portion and adapted to hold a rod-shaped aiming device which is secured by a set screw 28'. FIG. 12 shows the aiming device in position, as well as the X-ray equipment positioned above and below the fracture to be connected.

FIG. 8 likewise illustrates a first stage of an operation carried out by means of the device: after the connector plate has been inserted into the thigh through a small cut and has been slid into an approximate position as viewed by means of X-ray equipment and the aiming device; its correct location in relation to the neck portion is found by means of a guide wire 30 which is inserted into the bone material of the femur shaft and into the bone of the neck through an inner tubular guide (32) located within an outer tube 31 extending through the bore 26 of the connector arm into the screw-threaded bore 5 of the connector plate, The inner tubular guide 32 is screwed into bore 5 of the plate in order to permit exact centering of guide wire 30 and to prevent its disengagement from the connector plate, In case of incorrect location the guide wire is withdrawn, the connector plate is moved by means of the connector arm into another position and the guide wire is again inserted into the bone. In the case the location is found to be correct as seen by X-ray viewing, the pointed bar 24 is forcefully pushed into the bone to finally fix the position of bone and plate, whereupon the guide wire 30 and the inner tubular guide (32) are removed. They are replaced by the second inner tubular guide 32a of wider inner bore, and a drill 35 is inserted therethrough which, by mechanical rotation, drills holes into the shaft and the neck for subsequent insertion of one of the long screws.

Figure 11:
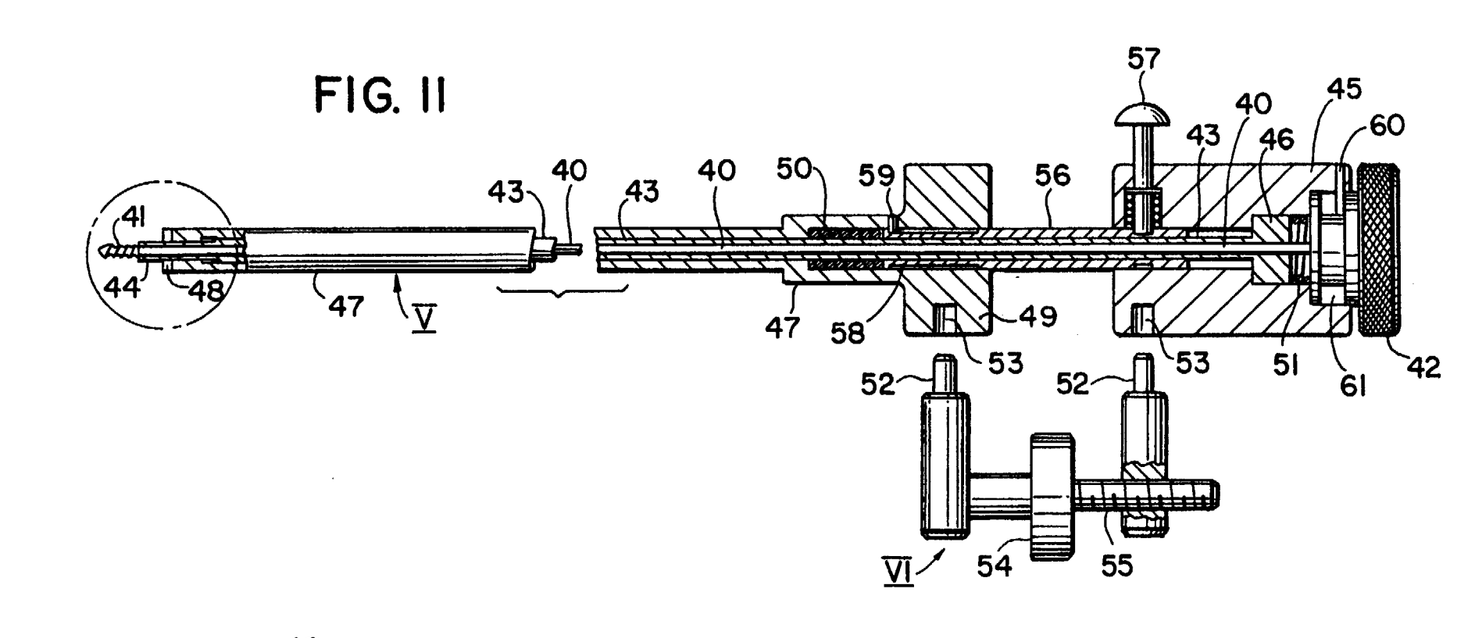
FIG. 11 is a longitudinal section through the screwdriver used in inserting the long screws and their sleeves.
Figure 11A:
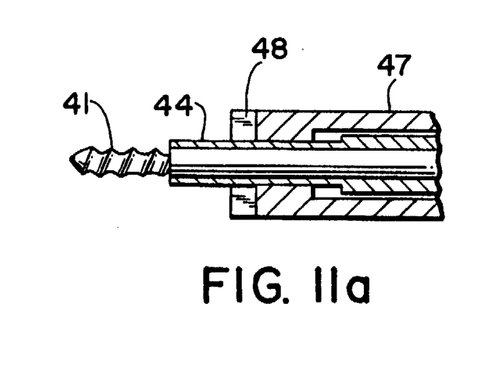
FIG. 11a is an enlarged section of the left hand end of the screwdriver of FIG. 11.
Figure 11B:
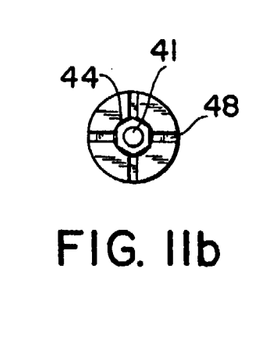
FIG. 11b is an end view of the screwdriver of FIG. 11.

The special screwdriver V as illustrated in FIG. 11 comprises three concentrically aligned shafts which are independently movable in both axial and rotary direction. They include:

1. an innermost shaft 40 with a screw-threaded end 41 suitable for engaging the bore 13 in the rear end of the long screws and for, rotation by a grip 42 at the outer end of the screw driver.
2. an inner tubular shaft 43 having a hexagon-shaped end 44 for engagement with the hexagonal recess 12 in the long screws. It can be rotated for driving the screw into the pre-drilled bone material by means of a cylindrical grip 45 via a disc 46 firmly mounted on the shaft 43.
3. An outermost tubular shaft 47 having an inner end in the form of cross-wise aligned edges 48 for engagement with slots 16 in the screw sleeves III. It can be rotated for the purpose of screwing the sleeves into the connector plate by means of a cylindrical grip 49.
4. An outer sleeve 56 rotationally and longitudinally movable on the inner movable shaft 43. It is provided with a circumferential recess 58 engaged by a pin 59 serving to limit the longitudinal motion of the shaft. A second circumferential recess is provided at the other end of sleeve 56 and engages a stop 57.

The components can be axially moved relative to each other, but are urged into their normal position by helical springs 50 and 51, while additional axial motion of the tubular shaft 43 is made possible by withdrawal of stop 57; their specific use will be explained further on in connection with the final stage of the operation.

The final stage of the operation of connecting a fractured head to the femur shaft is illustrated in FIG. 10, as follows:

After the bone has been drilled through the oblique bores the inner tubular guide is removed. Now the two long screw-and-sleeve assemblies are inserted and fastened, one after the other, with the aid of the screw driver V, as follows: a screw II is pulled back into a sleeve III up to its outer end, and the hexagon-shaped end 44 of the screwdriver is pushed into the correspondingly shaped recess 12 in the screw end. By rotating grip 42 and pushing it against the force of helical spring 51, the threaded end 41 of the innermost shaft 40 of the screw-driver is screwed into screw-threaded bore 13 of the screw, while the protruding edges 48 of the outermost tubular shaft 47 are urged into slots 16 in the end of sleeve III by means of helical spring 50. Additional tightening of the screwed end 41 into bore 13 connects and firmly secures the screw-and-sleeve assembly to the screwdriver. By means of the screwdriver the assembly is now pushed in an inward direction through the outer tubular guide 31, and rotated as far as the screw-thread on the sleeve III allows, and the sleeve is screwed into bore 5 of the connector plate by rotation of grip 49. By pulling out the stop 57, grip 45 which is connected to the inner shaft 43 by means of collar 46, can be moved in an inward direction thereby pushing shaft 43 inwardly. By rotating and pushing grip 45 inwardly, screw II is moved along sleeve III and is urged towards the fractured head portion and inserted into the pre-drilled bore in the bone material, rotation being stopped as soon as it has reached the required depth as viewed by X-ray equipment, or whenever step 17 on the screw has reached the crimped end 18 of the sleeve. A pin 60 engaging with a circumferential groove 61 limits the distance to which grip 42 can be moved in an outward direction, while being urged there by spring 51. In addition, during fracture compression pin 60 transfers the load from grip 45 to shaft 40 via grip 42. In order to pull the fractured head in the direction of the femur shaft and thus to compress the fracture, a retracting device VI is attached to the grips 45 and 49 by means of pins 52 inserted into corresponding holes 53. By rotating the handwheel 54, screw 55 pulls grips 49 and 45 apart as well as grip 42 (by means of pin 60), thereby pulling the attached screw II into the sleeve which is firmly screwed and secured in the plate. After insertion and fixation of the first screw, pointed bar 24 is removed and the second screw is inserted into the fractured parts in the same manner.

After insertion of both long screws, the connector plate is firmly attached to the femur shaft by means of two to three shorter screws 34. For this purpose a shorter tubular guide is inserted into the tissue through one of the bores 27 of the connector arm and secured by a set screw 28. Thereafter the bore is drilled in the conventional manner and a screw 33 is inserted with its head positioned in the countersink of the bore 7, preventing its protruding out of the plate. After all screws have been fixed, the connector arm is removed from the plate and out of the body by detaching screw 22, the skin incisions are closed and the wounds are dressed.

Figure 15:
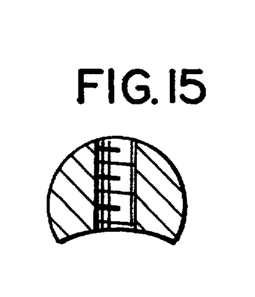
FIG. 15 is a section along line 15—15 of FIG. 14.
Figure 16:
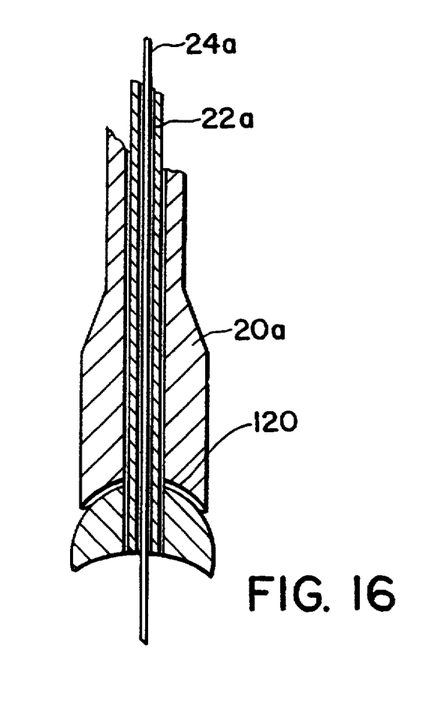
FIG. 16 is a section along line 16—16 of FIG. 8, showing connection of the connector plate of FIG. 13 to the connector arm.

FIGS. 13, 14, 15 and 16 show a simplified version of the connector plate illustrated in FIGS. 1 and 2. It differs from the earlier version by omission of the outwardly bent head portion 2, the two small bores 4 and of the two lugs 6, the other components being identical in both embodiments and marked by identical numerals but with the letter "a" appended thereto. The present connector plate has a thicker upper portion, while the lower portion is of about the same thickness as that shown in FIG. 1. Instead of the bent head portion the underside of the thickened upper portion is cut away at a slant (102) corresponding to the shape of the femur. The two lugs 6 appearing in FIG. 1 are necessary to permit a sufficient length of the screw thread 5, but owing to the greater thickness of the present plate there is sufficient material for these bores. The two bores 4 of FIG. 1 are necessary for connection to the connector arm by means of two pins engaging with the bores; the present connection is made by engagement of the concave end of the arm (120) with the rounded top surface of the connector plate (v. FIG. 15), thus keeping the two in firm and straight alignment.

Figure 17:
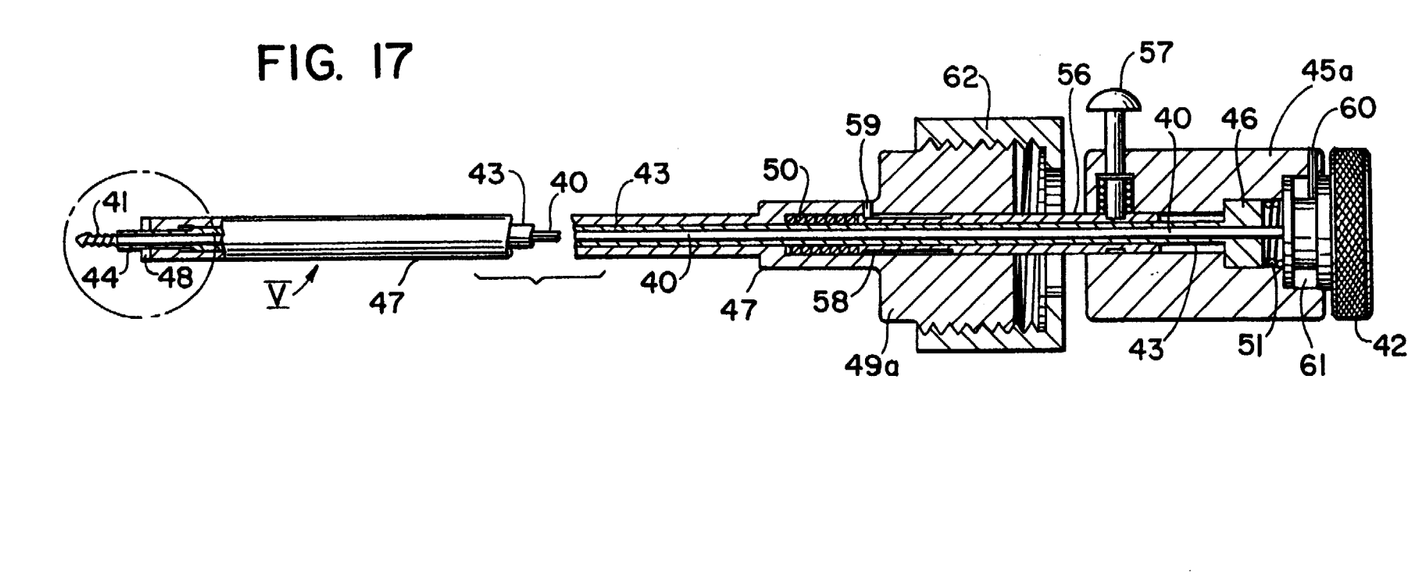
FIG. 17 is a longitudinal section of another embodiment of the screwdriver illustrated in FIG. 11.
Figure 17A:
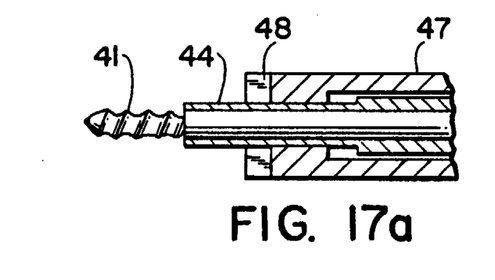
FIG. 17a is an enlarged section of the left hand end of the screwdriver of FIG. 17.
Figure 17B:
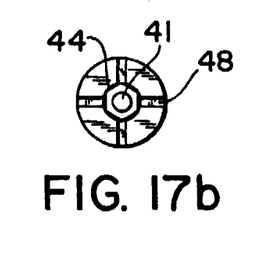
FIG. 17b is an end view of the screwdriver of FIG. 17.

A second version of the screwdriver V is illustrated in FIG. 17, wherein the means for moving the grips 49a and 45a apart is by means of a cup-shaped spacer 62. The spacer is provided with an inner screw-thread cooperating with an outer screw-thread on grip 49a. By rotation of the spacer it is moved to the rear until it contacts grip 45a and moves grip 42 via pin 60 to the rear, thereby pulling screw II rearwardly into the sleeve by means of screw 41 engaging the tapped bore 13 in the screw end, and thus compresses the fracture.

FIG. 12 illustrates the shape and use of an aiming device which is an additional feature of the invention. The device is used at the beginning of the operation to locate the optimal final position of the screws to be inserted into the fractured bone. It is attached to the connector arm 21 and is adjusted in the direction of the fracture from the outside of the thigh. By viewing the position of the aiming device in relation to the femoral neck by X-ray equipment (73,74) the position of the connector plate and the auxiliary equipment can be adjusted and brought into the most suitable location.

The aiming device comprises an aiming rod 70 connected to the end of a connecting bar 71 at right angles by clamping means 72. The connecting bar is held in position in the hole 29 at the bottom end of the connector arm 21 and secured there by means of the set screw 28'. After adjustment of the connector plate the aiming device can be detached. As known to the art, all further stages of the operation are likewise controlled by X-ray viewing.

It is reiterated that a few of the described stages of the afore described percutaneous operation resemble those described in my U.S. Pat. No. 4,465,065, but that most components of the present device have been changed and modified. The improvements over the surgical device described in my earlie patent are: fixation of the long screws in sleeves, permitting their axial sliding motion without protrusion out of the bone and soft tissue; ready insertion of the long screws by means of special tooling, and active compressing of the fracture after insertion of the long screws, again with the aid of the special screwdriver. In addition, modification of the connector plate enhances stability of the junction between plate and screw, while the temporary fixation of the plate to the femur by means of the pointed bar 24 ensures high accuracy in pre-drilling of the bone.

It will be understood that the outer shape and form of the different components, both permanent and auxiliary, have been designed with the object of performing the task in hand at maximum convenience for the surgeon and in a mimimum of time, by obviating change of tools and equipment as found necessary with conventional devices. However, they may be changed or modified as long as they will serve to perform the afore described steps of the operation, i.e. connecting and compressing the fractured parts for the benefit of the patient, while maintaining the percutaneous surgical technique.

What is claimed is:

1. A surgical device for percutaneous connection of a fractured upper part of a femur to a femur shaft of a patient, comprising the following components to remain in the body of the patient:

a bar-shaped connector plate having an axis, an inner surface to be placed onto the femur, an outer surface, a head portion and a bottom provided with a sharpened end for insertion of said bar-shaped connector plate through a small incision in the skin of the patient, said bar-shaped connector plate being provided in a lower portion thereof with at least two countersunk, through-going bores and in an upper portion thereof with two adjoining oblique, screw-threaded bores directed in an upward direction at an angle of about 130°, a screw-threaded bore perpendicular to the axis of said bar-shaped connector plate being provided in said head portion, two long screws, each screw having a straight shaft, a wood-screw-shaped inner end for insertion into said fractured upper part of the femur and an outer end coaxially recessed with a polygonal shape, said recess being continued by a screw-threaded bore concentric with an axis of said shaft, a sleeve of a shorter length than said screw, with the outer end of said screw being positioned in said sleeve in a manner so as to be movable in both axial and rotational directions in the sleeve, the sleeve having an outer end provided with a screw-thread corresponding to the screw thread in said oblique bores in said bar-shaped connector plate and with at least two recesses for engagement of a screwdriver, and at least two shorter screws for securing said bar-shaped connector plate to the femur shaft, said at least two shorter screws extending through said countersunk, through-going bores into bone material of the femur shaft.

2. Auxiliary equipment serving to insert and to connect to the fractured upper part of said femur and for use with the surgical device as defined in claim 1, comprising:

an angular connector arm including a short horizontal portion for connection to the head portion of said bar-shaped connector plate and a longer vertical portion extending parallel to the lower portion of said bar-shaped connector plate, wherein said horizontal portion is provided with an axial perforation for passage of a screw engaging with said screw-threaded bore in said head portion of said bar-shaped connector plate and is shaped to conform to the shape of said head portion to ensure absolute parallelism of said vertical portion with said bar-shaped connector plate, and wherein said vertical portion is provided with two adjoining obliquely directed bores coaxially aligned with said two oblique screw-threaded bores in said plate, and with at least two straight bores coaxially aligned with said at least two countersunk, through-going bores in said plate, a first tubular guide of an outer diameter cooperating with said oblique bores in said angular connector arm and of an inner diameter corresponding to an outer diameter of said sleeve covering said long screw, of a length compatible with a distance between the respective oblique bores in said plate and said angular connector arm, a first removable tube for insertion into said first tubular guide and having a bore with an inner diameter corresponding to an outer diameter of a guide wire to be pushed therethrough into said fractured upper part, a second removable tube for insertion into said first tubular guide and having a bore with an inner diameter corresponding to a diameter of a drill for predrilling said femur, a guide wire to be pushed through the bore in said first removable tube, a drill to be inserted into the bone material through the bore in said second removable tube, a second tubular guide for insertion into said straight bores in said angular connector arm, of a length compatible with the distance to said bar-shaped connector plate, and of an inner diameter suitable for the passage of a drill destined for predrilling the bone material for acceptance of said shorter screws, a screw-driver for insertion and fixation of said long screws, said screw-driver comprising:

an inner shaft provided with a screw-threaded inner end for engagement with said screw-threaded bore in the recessed end of said long screw, a median tubular shaft provided with a polygonal inner end for engagement with said polygonal recess in said long screw, and an outer tubular shaft provided at an inner end thereof with protruding teeth for engagement with said recesses in said sleeve covering said long screw, wherein all three shafts are independently movable in both axial and rotational directions by grips attached to outer ends thereof, and wherein helical springs are provided to adjust axial alignment of the respective shafts.

3. The surgical device as defined in claim 2, wherein said vertical portion of said angular connector arm is provided with set screws serving to secure said tubular guides.

4. The surgical device as defined in claim 2, wherein a lower end of the vertical portion of said angular connector arm is provided with means for holding a rod-shaped aiming device.

5. The surgical device as defined in claim 4, wherein said aiming device comprises an aiming rod connected at right angles to a connecting bar, said connecting bar being adapted to be attached to the lower end of said vertical portion of said angular connector arm by means permitting adjustment of the angular direction of said aiming bar.

6. The surgical device as defined in claim 2, wherein said screwdriver is provided with means for pulling the screw-threaded end of said inner shaft into said outer tubular shaft, serving to pull said long screw in an outward direction relative to said sleeve.

7. The surgical device as defined in claim 2, wherein said screwdriver is provided with an outer sleeve held in position by a removable pin and engaging said outer tubular shaft by means of a pin movable along a circumferential recess on an outside of said outer sleeve.

8. The surgical device as defined in claim 2, further including a screw extending through said horizontal portion of said angular connector arm, said screw being provided with a grip at an outer end thereof and being centrally perforated permitting the passage of a sharp pin to be pushed into the bone material for exact fixation of said angular connector arm.

9. The surgical device as defined in claim 2, wherein said head portion of said bar-shaped connector plate is convex, and an end of said horizontal portion of said angular connector arm is concave to correspond with the convex head portion of said bar-shaped connector plate.

10. The surgical device as defined in claim 1, wherein an outer portion of said bar-shaped connector plate surrounding said oblique screw-threaded bores is thickened in the form of two oblique lugs protruding out of the outer surface of the bar-shaped connector plate.

11. The surgical device as defined in claim 1, wherein the head portion of said bar-shaped connector plate is bent outwardly to conform to the contour of the femur, and wherein said head portion is perforated by said screw-threaded bore and by at least one smooth bore, both bores being perpendicular to the axis of said bar-shaped connector plate.

12. The surgical device as defined in claim 1, wherein the inner surface of said headportion of said bar-shaped connector plate slopes outwardly in accordance with the contour of said femur.

13. The surgical device as defined in claim 1, wherein the outer surface of the head portion of said bar-shaped connector plate is convex.

14. The surgical device as defined in claim 13, wherein an end of said horizontal portion of said angular connector arm is concave to correspond with the convex head portion of said bar-shaped connector plate.

15. The surgical device as defined in claim 1, wherein each of said long screws is provided with a circumferential step, and wherein each said sleeve has an inner end which is inwardly crimped, to prevent said screw from sliding out of said sleeve, due to contact of said step with said crimped end.

16. The surgical device as defined in claim 1, wherein said polygonal shape is a hexagon.

* * * * *